US010874705B2

(12) United States Patent
Shafeek et al.

(10) Patent No.: US 10,874,705 B2
(45) Date of Patent: Dec. 29, 2020

(54) **EXTRACTS AND ISOLATED COMPOUNDS FROM *CAKILE ARABICA* FOR TREATMENT OF ULCER**

(71) Applicant: KING SAUD UNIVERSITY, Riyadh (SA)

(72) Inventors: Awaad Amani Shafeek, Riyadh (SA); Reham Moustafa El-Meligy, Riyadh (SA); Mohammed Sobhy Marzouk, Riyadh (SA); Shroog Mohamed Alotaiby, Riyadh (SA)

(73) Assignee: King Saud University

( * ) Notice: Subject to any disclaimer, the term of this patent is extended or adjusted under 35 U.S.C. 154(b) by 498 days.

(21) Appl. No.: 15/422,614

(22) Filed: Feb. 2, 2017

(65) Prior Publication Data
US 2017/0143782 A1  May 25, 2017

Related U.S. Application Data

(62) Division of application No. 14/477,026, filed on Sep. 4, 2014, now abandoned.

(30) Foreign Application Priority Data

Sep. 12, 2013  (EP) .................................. 13184046

(51) Int. Cl.
| | | |
|---|---|---|
| *A61K 36/31* | (2006.01) | |
| *A61K 31/20* | (2006.01) | |
| *A61K 31/22* | (2006.01) | |
| *C07C 51/42* | (2006.01) | |
| *A61K 31/225* | (2006.01) | |
| *C07C 67/56* | (2006.01) | |
| *C07C 51/47* | (2006.01) | |
| *A61K 9/00* | (2006.01) | |
| *B01D 11/02* | (2006.01) | |
| *B01D 15/42* | (2006.01) | |
| *C07C 67/58* | (2006.01) | |
| *C11B 1/10* | (2006.01) | |

(52) U.S. Cl.
CPC ............ *A61K 36/31* (2013.01); *A61K 9/0053* (2013.01); *A61K 31/20* (2013.01); *A61K 31/22* (2013.01); *A61K 31/225* (2013.01); *B01D 11/0288* (2013.01); *B01D 11/0292* (2013.01); *B01D 15/426* (2013.01); *C07C 51/42* (2013.01); *C07C 51/47* (2013.01); *C07C 67/56* (2013.01); *C07C 67/58* (2013.01); *C11B 1/10* (2013.01); *A61K 2236/00* (2013.01); *A61K 2236/33* (2013.01)

(58) Field of Classification Search
None
See application file for complete search history.

(56) References Cited

U.S. PATENT DOCUMENTS

2003/0021850 A1*  1/2003  Xu ..................... A61K 31/20
424/520

FOREIGN PATENT DOCUMENTS

| JP | S56154414 A | 11/1981 |
|---|---|---|
| KR | 2010 0111040 A | 10/2010 |

OTHER PUBLICATIONS

J. Bornmuller, "Über eine neue Cakile-Art aus der Flora Arabiens: Cakile Arabica Velenovsky et Bornmuller" Reportorium Novarum Specierum Regni Vegetabilis, vol. 9, No. 7-9, Jan. 1, 1911, pp. 114-114 ISSN: 0375-121X (English translation not available).
CID 16088229—PubChem "Phellodrenic Acid A".
European Search Report for EPO Appln. No. 13184046.4 dated Dec. 4, 2013.

* cited by examiner

*Primary Examiner* — Terry A McKelvey
*Assistant Examiner* — Catheryne Chen
(74) *Attorney, Agent, or Firm* — Renner, Kenner; Arthur M. Reginelli

(57) ABSTRACT

The present invention relates to extracts, compounds isolated from *Cakile arabica* for use in the treatment of ulcer and to pharmaceutical compositions thereof.

14 Claims, No Drawings

EXTRACTS AND ISOLATED COMPOUNDS FROM *CAKILE ARABICA* FOR TREATMENT OF ULCER

This application is a divisional application of U.S. non-provisional application Ser. No. 14/477,026 filed on Sep. 4, 2014, which claims priority to European Patent application no. 13184046.4 filed on Sep. 12, 2013, which are incorporated herein by reference.

The present invention relates to extracts from *Cakile arabica*, compounds isolated from *Cakile arabica* and their use for the treatment of ulcer.

The importance of natural resources (of botanical and/or animal origin) is nowadays receiving a great deal of concern from scientists all over the world.

The Arab world has not heritage in the field of medicinal plants. In fact, this heritage goes back as far as the Chinese heritage, if not even older. However, in China as well as in Japan, they were able by systematic studies and applying modern technology, to explore their natural resources of medicinal plants so that more than 80% of their diseases are now treated by what they call "traditional medicine".

Medicinal plants from traditional healers revealed 73 plant species being used as wound healing remedies, according to the definitions of wounds given by the healers themselves. The plants, belonging to 34 plant families, are used as first aids, in the washing of wounds, extraction of pus, as coagulants, as well as for infected wounds. Some others can be a rich source of potential antiviral compounds.

Crucifereae is a large family consist of from 3200 species in 375 genera, it is also known recently as the Brassicaceae. It includes vegetable crops, medicinal plants and plants uses as food. Veral plants of this family are used medically as antidiabetic, antibacterial, antifungal, anticancer, antirheumatic and insecticidal.

Nutrition benefit of Crucifers species have been very important source of oil and proteins for animal and human nutrition. In addition to the nutritional benefits, they constitute a very rich source of health-promoting phytochemical such as phenols, flavonoids, phenylpropanoids, vitamins, glucosinolates, fibres, soluble sugars, fats and carotenoids. Besides this, there is growing evidence that a higher intake of *Brassica* vegetables (e.g., broccoli, cabbage, kale, mustard greens, Brussels-sprouts, cauliflower) could help to reduce the risk of cancer.

Crucifers contain many bioactive components including flavonoids (e.g. quercetin), glucosinolates (GLS). Among the most-studied bioactive compounds in crucifers associated with cancer protection are glucosinolates.

Flavonoids are involved in a vast array of biological functions. Quercetin, a major representative of the flavonol subclass and which is helps in the prevention of cancer, atherosclerosis and chronic inflammation. Furthermore, isorhamnetin isolated from mustard leaf showed a strong activity in reducing serum levels of glucose in *Diabetes mellitus* through an antioxidant activity test.

Other phenolic compounds as sinapoyl esters and proanthocyanidins (condensed tannins) are considered undesirable compounds in human nutrition.

Naturally, the wide range of glucosinolates content among different groups of *B. oleracea* would result in significant differences in their health-promoting properties.

Peptic ulcer is a common gastrointestinal disorder in modern era. It becomes a common global health problem affecting a large number of people worldwide. There are different classes of drugs that have been used in the treatment of peptic ulcer, most of them exhibits serious side effects like; arrhythmias, gynaecomastia, arthralgia and hypergastrinemia (Awaad et al. Journal of Saudi Chemical Society 2013, 17, 101-124).

It is an object of the present invention to provide novel and efficient agents for the treatment of ulcer which overcome drawbacks of the prior art by having less side effects and which, particularly, can be obtained from natural materials.

This object is achieved by an extract from a plant material of *Cakile arabica* for use in the treatment of ulcer.

Preferably, the extract is an alcoholic extract, more preferably is an ethanolic extract.

Most preferred, the plant material comprises the aerial parts of *Cakile arabica*.

The object is further achieved by a compound selected from tetracosanoic acid and/or 4-hydroxy-5-n-butoxy-5-oxopentanoic acid for use in the treatment of ulcer The object is also achieved by a method for isolating tetracosanoic acid and/or 4-hydroxy-5-n-butoxy-5-oxopentanoic acid from *Cakile arabica*, comprising the steps:
a) extracting a plant material of *Cakile arabica* to obtain an extract;
b) concentrating the extract to obtain a concentrate;
c) chromatographing the concentrate into fractions; and
d) isolating fractionated compounds.

It is preferred that the plant material comprises the aerial parts of *Cakile arabica*.

Furthermore, it is preferred that extracting is carried out by using at least one organic solvent.

In a preferred embodiment, the organic solvent is selected from the group consisting of petroleum ether, heptane, hexane, ethanol, isopropanol, methanol and mixtures thereof, preferably is ethanol.

Most preferred, chromatographing is carried out by means of thin layer chromatography (TLC) and/or column chromatography.

Preferably, the eluent used for chromatographing is petroleum ether, heptane, ethanol, methanol, benzene, diethyl ether, chloroform, dichloromethane, water and/or mixtures thereof.

It is further preferred that the stationary phase used for chromatographing is silica gel and/or aluminum oxide.

Finally, the object is achieved by a pharmaceutical composition comprising the inventive extract and/or at least one of the inventive compounds.

Preferably, the composition is formulated for oral administration.

Surprisingly, it was found that extracts from *Cakile arabica* as well as compounds isolated thereof solve the problem by providing natural agents for the treatment of ulcer which exhibit similar or even higher anti-ulcer activity compared to drugs known from the prior art. Further, it was found that the extract and compounds can be used for the treatment of ulcer with no side effects on the liver and kidney functions.

Further, it was surprisingly found that several compounds having anti-ulcer activity can be isolated from *Cakile arabica* by the inventive method in an easy and efficient way.

"Extracting" in terms of the present invention, for preparing the inventive extract or in the first step of the inventive method, can comprise only one or more than one consecutive extraction steps. In the latter case, different solvents or solvent mixtures, in particular solvents or solvent mixtures having a significantly different polarity, can be used in the varioius steps.

In the same way, "chromatographing" in terms of the present invention can comprise only one chromatographic separation as well as more than one consecutive chromatographic separation steps. Particularly, different eluents and/or stationary phases can be used in each chromatography step. Further, in case that two or more chromatographic separation steps are carried out, each step can be a different chromatographic method, for example in the first step a mixture (concentrate) is separated by column chromatography and single fraction obtained in the first step is subsequently separated by thin layer chromatography.

The term "pharmaceutical composition", as used herein, is intended to comprise at least one pharmaceutically active extract of the present invention and/or at least one of the isolated compound of the present invention and/or corresponding salts thereof.

The pharmaceutical composition can be, for example, in a liquid form, e.g. a solution, sirup, elixir, emulsion and suspension, or in a solid form, e.g. a capsule, caplet, tablet, pill, powder and suppository. Granules, semi-solid forms and gel caps are also considered. In case that the pharmaceutical composition is a liquid or a powder, dosage unit optionally is to be measured, e.g. in the dosage unit of a teaspoon. In addition to one of the extracts or the isolated compounds, the pharmaceutical composition can comprise, for example, flavoring agents, sweeteners, dyes, stabilizers, diluents, suspending agents, granulating agents, lubricants, binders and disintegrating agents. A tablet, for example, can be coated. All of the formulations mentioned can be intended for immediate-release, timed-release and sustained release.

All components of the pharmaceutical composition have to be pharmaceutically acceptable. The term "pharmaceutically acceptable" means at least non-toxic. The therapeutically active compound should preferably be present in the above-mentioned pharmaceutical composition in a concentration of about 0.1 to 99.5% by weight, preferably of about 0.5 to 95% by weight of the total mixture.

The above-mentioned pharmaceutical composition can further contain other pharmaceutical active compounds in addition to the active extracts and/or compounds according to the invention.

Without limiting its scope, the invention can be summarized in terms of the following very preferred embodiment with reference to the surprisingly found inventive effect.

Two carboxylic acid derivatives were isolated from *Cakile arabica* for the first time and were identified as tetracosanoic acid 1 and 4-hydroxy-5-n-butoxy-5-oxopentanoic acid 2. The total alcohol extract (1000 mg/kg) and the isolated compounds (50 mg/kg) showed potent anti-ulcerogenic activity in absolute ethanol-induced ulcer model in rats with respect to ranitidine (100 mg/kg) as a reference standard drug. The total alcohol extract (TAE) was the very effective agent in this study, where it showed 98.5% protection of control ulcer followed by 1 and 2 at the dose of 50 mg/kg, which produced 80%, and 55.5%, respectively in comparison with 46.2% exerted the standard ranitidine (100 mg/kg). The acute toxicity study showed that the TAE was highly safe as the $LD_{50}$ was more than 4000 mg/kg, and these results were well supported by the sub-chronic toxicity, as the TAE administered to rats for 15 consecutive days at dose 1000 mg/kg showed no alteration in the liver and kidney functions.

Additional features and advantages of the present invention will become apparent in the following detailed description on the basis of the examples.

EXAMPLES

Materials and Methods:
Plant Material:

Arial parts of *Cakile arabica* were collected during flowering stage in March 2012 from Riyadh territory, the sample was identified by Dr. Jacob Thomas; assistant professor of taxonomy, Botany and Microbiology Department, Faculty of Science, King Saud University, and specimen were kept in the herbarium of Chemistry Department.

Samples of the aerial parts were air dried in shade, reduced to fine powder and kept for phytochemical and biological investigation.

Apparatus:

Melting points were determined on a Kofler hot-stage apparatus and are uncorrected.

Mass spectra (Electrospray negative ion) were taken from samples dissolved in acetonitrile with a Micromass Quattro spectrometer.

$^1$H- and $^{13}$C-NMR spectra, using external electronic referencing through the deuterium resonance frequency of the solvent, were determined at 600.17 or 150.91 MHz respectively with a JEOL ECA600 NMR spectrometer fitted with an auto-tune 5 mm X/H probe. Carbon atom types were established in the $^{13}$CNMR spectrum by employing a combination of broad-band proton-decoupled and DEPT (90 and 135) experiments. $[^1J_{C-H}]$, $[^2J_{C-H}]$ and $[^3J_{C-H}]$ $^1$H-$^{13}$C correlations were determined by using HMQC and HMBC pulse sequences. $^1$H-$^1$H correlations were determined by double quantum filtered COSY.

Pye Unicam pu 8800 spectrophotometer was used for UV spectral analysis.

Amino acid analysis was carried out using the amino acid analyzer (Eppendorf-LC 3000).

IR spectra were taken with a Shimadzu—IR-435 infrared spectrophotometer.

Phytochemical Screening:

Powdered samples of the aerial parts of *E. granulata* were subjected to preliminary phytochemical screening according to the published methods (Awaad, 2009).

Example 1

Extraction and Isolation:
Extraction of Plant Material:

Air-dried powder (1 kg) of *Cakile arabica* (aerial parts) was extracted by percolation in ethanol 95 for two days and filtered off (this process was repeated for three times). The combined alcohol portions were concentrated under reduced pressure at a temperature not exceeding 25° C. to yield a dry extract of 170 g.

Isolation:

An amount of 10 g dry TAE was dissolved in methanol and mixed with alumina for column chromatography. The solvent was evaporated on steam bath with continuous stirring to form a free flowing powder. The powder was then applied on the top of glass column (150×2.5 cm) packed with alumina (300 g). Elution was performed using a stop-gradient system with benzene-ethyl acetate. 100 fractions were collected (50 ml each) and reduced to three sub-groups after chromatographic examination using solvent system-a: benzene-ethyl acetate (86:14).

Sub-fraction I (2.50 g) contained two spots with $R_f$ values=0.66 and 0.60 (system a, TLC). It was fractionated on an alumina column (120 g, 1×90 cm) for separation of these two compounds that eluted with benzene-ethyl acetate 9:1 v/v. 20 fractions were collected and concentrated using rotary evaporator to obtain one compound which re-purified by re-crystallization from methanol to get compound 1.

Sub-fraction II (3.5 g) contained one spot with $R_f$-value=0.51 (system a, TLC). The solvent was evaporated using high pressure at low temperature to obtain 2.

Tetracosanoic Acid (1):

It was isolated as white amorphous powder (220 mg); mp 78-79° C.; $R_f$-value=0.56 (system: benzene-ethyl acetate, 90:10 v/v). IR $\nu_{max}$ (KBr, cm$^{-1}$) 3415, 2918, 2849, 1709, 1463, 720; $^1$H NMR (500 MHz, CDCl$_3$): δppm 2.32 (2H, t, J=7 Hz, H-2), 1.61 (2H, pentet-like, J=7 Hz, H-3), 1.23 (40H, br s, H-4 to H-23), 0.86 (3H, t, J=6.5 Hz, H-24); $^{13}$C NMR (125 MHz, CDCl$_3$): δppm 177.0 (C-1), 34.0 (C-2), 31.9 (C-3), 29.7 (C-4-16), 29.6 (C17), 29.5 (C-18), 29.4 (C-19), 29.3 (C-20), 29.1 (C-21), 24.7 (C-22), 22.7 (C-23), 14.2 (C-24).

The structure of 1 was established as tetracosanoic acid according to its chemical and physicochemical data (IR, $^1$H and $^{13}$C NMR) given above and confirmed by DEPT and H,H-COSY, HSQC and HMBC 2D-NMR correlation experiments.

4-Hydroxy-5-n-Butoxy-5-Oxopentanoic Acid (2):

It was isolated as white crystals (320 mg); $R_f$-value=0.45 (system: chloroform-methanol 90:10 v/v, TLC); bp 99-100° C.; IR $\nu_{max}$ (KBr, cm$^{-1}$): 3415, 2918, 2849, 1709, 1463, 720; NMR (500 MHz, CDCl$_3$): δppm 4.21 (1H, dd, J=7.8, 5 Hz, H-4), 4.10 (1H, t, J=6.25, 5 Hz, H-1'), 2.45 (1H, m, H-3), 2.31 (1H, m, H-2), 2.16 (1H, m, H-3'), 1.58 (2H, pentet-like, J=7.1 Hz, H-2'), 1.33 (2H, sixtet-like, J=7.3 Hz, H-3'), 0.88 (3H, t, J=7.3 Hz, H-4'); $^{13}$C NMR (125 MHz, CDCl$_3$): δppm 178.5 (C-1), 172.3 (C5), 65.3 (C-1'), 55.6 (C-4), 30.5 (C-2'), 29.3 (C-2), 24.8 (C-3), 19.0 (C-3'), 13.6 (C-4'). The structure of 2 was established by chemical and physicochemical data (IR, $^1$H and $^{13}$C NMR) given above and confirmed by DEPT and H,H-COSY, HSQC and HMBC 2D-NMR correlation experiments.

The isolated compounds were identified using different physical and spectral methods; melting point, UV and IR spectra, $^1$H-NMR, $^{13}$C-NMR, DEPT and correlation 2D NMR as 1 and 2.

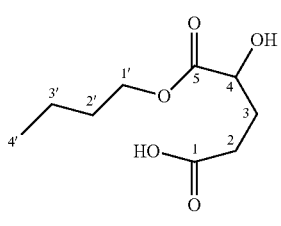

4-Hydroxy-5-n-butoxy-5-oxopentanoic acid (2)

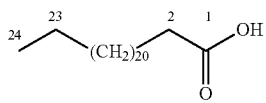

Tetracosanoic acid (1)

Example 2

Pharmacological Study

Animals:

Swiss albino mice of both sex (26-30 g) and male Wistar rats (180-200 g) were supplied by the animal house of King Saud University, KSA. Animals were housed in standard polypropylene cages with wire mesh top and maintained under standard conditions (temperature 23±1.0° C., humidity 55±10%, 12 h light/12 h dark cycle). They fed with a standard pellet diet with water ad libitum and were allowed to adapt to the laboratory environment for one week before experimentation.

Pharmacological Activities

1. Preparation of the TAE

Dried aerial parts of *Cakile arabica* (100 g) were extracted by percolation in 90% ethanol at room temperature for two days. The ethanol extract was filtered and the residues were re-percolated for four times. The total ethanol extract was concentrated under reduced pressure at a temperature not exceeding 35° C. to yield a dry extract of 25 g. The dried plant extract was freshly suspended in distilled water just before administration by the aid of Tween 80.

2. Determination of Median Lethal Dose ($LD_{50}$).

The oral median lethal dose ($LD_{50}$) of the TAE determined as described by Lorke Arch. Toxicology, 1983, 54, 251-287. Swiss albino mice in groups of six, received one of 500, 1000, 2000, or 4000 mg/kg doses of the tested TAE. Control animals were received the vehicle and kept under the same conditions. Signs of acute toxicity and number of deaths per dose within 24 h were recorded.

3. Anti-Ulcerogenic Activity:

Evaluation of the anti-ulcerogenic activity was carried out using absolute ethanol-induced ulcer model as described by Muthu et al. Int. J. Pharm. Pharm. Sci. 2013, 5, Suppl 1, 269-272.

About 30 Wistar rats were used, they divided into 5 groups each of 6 rats. Group 1 received the vehicle and served as control group, group 2 received ranitidine (100 mg/kg) and served as standard group, groups 3 received the total alcohol extract of the plant under investigation at a dose of 1000 mg/kg. groups 4 and 5 received the isolated compounds 1 and 2 at dose 50 mg/kg respectively.

Rats of all groups were fasted for 24 h then all medications were administered orally. One hour after treatment, the animals received an oral dose of absolute ethanol (1 ml/200 g) and then sacrificed one hour later, by ether inhalation, the stomachs were rapidly removed, opened along their greater curvature and gently rinsed under running tap water.

Number of lesions in the glandular part of the stomach were measured under an illuminated magnifying microscope (10×). Long lesions were counted and their lengths were measured. Petechial lesions were counted, and then each five petechial lesions were taken as 1 mm of ulcer.

The Lesion Scores:

the mucosal lesions were quantified by the scoring system (0-5) 0=no damage, 1=Local edema and inflammation without ulcers; 2=One ulcer without inflammation; 3=one to two ulcers with inflammation & lesion diameter <1 cm; 4=More than two ulcers with lesion diameter 1-2 cm; 5=Sever ulceration with lesion diameter >2 cm.

Ulcer Index

To calculate the ulcer index (mm), the sum of the total length of long ulcers and petechial lesions in each group of rats was divided by its number. The curative ratio was determined according to the formula:

% Protection of control ulcer=Control UI−Test UI/Control UI×100

4. Effect on Liver and Kidney Functions:

Male Wister rats were divided into 2 equal groups each of 10 rats. The 1$^{st}$ group was left as a control and administrated water orally, while the 2$^{nd}$ group was orally given the TAE in a dose of 1000 mg/kg for 15 days. Blood samples were collected from the orbital plexus of rats, 6 hr after the last dose. Samples were left to clot at room temperature for 30 min then centrifuged at 1000 rpm for 20 min.

The collected sera were used for determination of the activity of both (AST) aspirate aminotransferase and (ALT) alanine aminotransferase as a liver markers. In addition, levels of blood urea, serum creatinine were also estimated as a kidney markers (Awaad et al., Phytother. Res. 2013, 27, 126-130).

Biological Activities

1. Determination of Median Lethal Dose ($LD_{50}$).

The total alcohol extract *Cakile arabica* did not produce any behavioral changes or mortality in treated mice in doses up to 4000 mg/kg. Therefore, the tested plant can be categorized as highly safe since substances possessing $LD_{50}$ higher than 50 mg/kg are non-toxic (Soliman, Pharmaceutical Biology, 2012, 50(1) 105-112).

2. Anti-Ulcerogenic Activity.

The present results showed that the TAE at dose levels of 500 and 1000 mg/kg possessed a potent anti-ulcerogenic activity against ulcer-induced by absolute alcohol. It produced a percent protection of control ulcer by 44.6% and 98.5% respectively. The isolated compounds 1 and 2 (50 mg/kg), showed significant anti-ulcerogenic activity they produced percent protection of control ulcer by 80 & 55.3% respectively which are more effective than ranitidine which produce 44.6%. 1 was the most effective compound in the present study, it produced percent protection of control ulcer by 80% and it was mainly responsible for the activity of the investigated plant. (Table 1).

TABLE 1

Antiulcerogenic effect of TAE and isolates 1 and 2 from *Cakile arabica*

| Groups | Dose mg/kg | score | No. of ulcers | ulcer index | % protection |
|---|---|---|---|---|---|
| Control |  | 4 | 14 ± 2.35 | 13 ± 2.24 |  |
| Ranitidine | 100 | 2.2 | 7.2 ± 0.84*** | 7 ± 1.58** | 46.2 |
| TAE-1000 | 1000 | 0.2 | 0.2 ± 0.45*** | 0.2 ± 0.45*** | 98.5 |
| 1 | 50 | 1 | 2 ± 2.74*** | 2.6 ± 3.58*** | 80 |
| 2 | 50 | 2 | 3.6 ± 2.97*** | 5.8 ± 3.42** | 55.3 |

Data are expressed as mean ± SD, n = 6, *p ≤ 0.05, p ≤ 0.01, *p ≤ 0.001

3. Liver and Kidney Functions:

Both liver and kidney functions were not affected after treatment of TAE (1000 mg/kg) for 2 weeks, as there is no significant difference between control and test group in all experiments, at the 0.05 level of probability (Table 2).

TABLE 2

Effect of TAE on liver and kidney functions of rats.

| Groups | ALT (U/l) | AST (U/l) | Blood Urea (mg/dl) | Serum Creatinine (mg/dl) |
|---|---|---|---|---|
| Control | 4.8 ± 0.37 | 5.2 ± 0.37 | 45.50 ± 1.36 | 0.82 ± 0.02 |
| TAE-1000 | 5.1 ± 0.22 | 5.3 ± 0.39 | 46.00 ± 1.9 | 0.84 ± 0.02 |

Data are expressed as mean ± SD, n = 10

These results showed that, the alcohol extract of the investigated plant didn't reveal hepatotoxic manifestation. In addition, no apparent nephrotoxic manifestations were recorded; this indicated that no side effects were obtained the alcohol extract of *Cakile arabica*.

The features disclosed in the foregoing description and claims may both separately and in any combination be material for realizing the invention in diverse forms thereof.

The invention claimed is:

1. A method for treating an ulcer, the method comprising: orally administering to a patient an extract from a plant material of *Cakile arabica*, wherein the extract includes 4-hydroxy-5-n-butoxy-5-oxopentanoic acid and tetracosanoic acid.

2. The method of claim 1, wherein the extract is an alcoholic extract.

3. The method of claim 2, wherein the extract is an ethanolic extract.

4. The method of claim 1, wherein the plant material comprises the aerial parts of *Cakile arabica*.

5. The method of claim 1, wherein the extract includes tetracosanoic acid and 4-hydroxy-5-n-butoxy-5-oxopentanoic acid.

6. The method of claim 1, wherein said step of orally administering includes orally administering a pharmaceutical composition that includes the extract from a plant material of *Cakile arabica*.

7. The method of claim 6, where the pharmaceutical composition is in the form of a liquid or a solid.

8. A method for treating a ulcer, the method comprising: orally administering 4-hydroxy-5-n-butoxy-5-oxopentanoic acid or 4-hydroxy-5-n-butoxy-5-oxopentanoic acid and tetracosanoic acid, where said tetracosanoic acid and 4-hydroxy-5-n-butoxy-5-oxopentanoic acid are obtained by
   (a) extracting a plant material of *Cakile arabica* to obtain an extract;
   (b) concentrating the extract to obtain a concentrate;
   (c) chromatographing the concentrate into fractions; and
   (d) isolating fractionated compounds.

9. The method according to claim 8, wherein the plant material comprises the aerial parts of *Cakile arabica*.

10. The method according to claim 8, wherein extracting is carried out by using at least one organic solvent.

11. The method according to claim 10, wherein the organic solvent is selected from the group consisting of petroleum ether, heptane, hexane, ethanol, isopropanol, methanol and mixtures thereof, preferably is ethanol.

12. The method according to claim 8, wherein chromatographing is carried out by means of thin layer chromatography (TLC) and/or column chromatography.

13. The method according to claim 12, wherein the eluent used for chromatographing is petroleum ether, heptane, ethanol, methanol, benzene, diethyl ether, chloroform, dichloromethane, water and/or mixtures thereof.

14. The method according to claim 8, wherein the stationary phase used for chromatographing is silica gel and/or aluminum oxide.

* * * * *